(12) United States Patent
Mosebach et al.

(10) Patent No.: US 12,102,809 B2
(45) Date of Patent: Oct. 1, 2024

(54) DRUG DELIVERY DEVICE WITH AUDIBLE INDICATOR SPRING

(71) Applicant: SANOFI-AVENTIS DEUTSCHLAND GMBH, Frankfurt am Main (DE)

(72) Inventors: Carsten Mosebach, Frankfurt am Main (DE); Thomas Mark Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 508 days.

(21) Appl. No.: 17/129,111

(22) Filed: Dec. 21, 2020

(65) Prior Publication Data

US 2021/0146053 A1 May 20, 2021

Related U.S. Application Data

(63) Continuation of application No. 15/578,881, filed as application No. PCT/EP2016/062504 on Jun. 2, 2016, now Pat. No. 10,888,669.

(30) Foreign Application Priority Data

Jun. 3, 2015 (EP) .................................. 15170583

(51) Int. Cl.
*A61M 5/315* (2006.01)
*A61M 5/20* (2006.01)
(Continued)

(52) U.S. Cl.
CPC ........ *A61M 5/3157* (2013.01); *A61M 5/2033* (2013.01); *A61M 5/24* (2013.01);
(Continued)

(58) Field of Classification Search
CPC .............. A61M 5/2033; A61M 5/3157; A61M 2005/2013; A61M 2005/206;
(Continued)

(56) References Cited

U.S. PATENT DOCUMENTS 5,483,953 A * 1/1996 Cooper .................... F15D 1/00
128/203.29
8,652,100 B1 2/2014 Cowe
(Continued)

FOREIGN PATENT DOCUMENTS

CN 103143082 6/2013
CN 104080499 10/2014
(Continued)

OTHER PUBLICATIONS

PCT International Search Report and Written Opinion in International Application No. PCT/EP2016/062504, dated Jul. 15, 2016, 8 pages.
(Continued)

*Primary Examiner* — Kami A Bosworth
(74) *Attorney, Agent, or Firm* — Fish & Richardson P.C.

(57) ABSTRACT

A drug delivery device including a case adapted to hold a medicament container, a plunger disposed within the case and slidable from a proximal position into a distal position for delivering a medicament from the medicament container, and an audible indicator that is arranged within a case pocket lateral to the plunger and that is in operative connection with the plunger. The audible indicator includes at least one indicator spring and at least one locking element, where the indicator spring is biased by the locking element, and the indicator spring relaxes due to a release of the locking element by a movement of the plunger.

22 Claims, 3 Drawing Sheets

(51) Int. Cl.
*A61M 5/24* (2006.01)
*A61M 5/32* (2006.01)

(52) U.S. Cl.
CPC ...... *A61M 5/31505* (2013.01); *A61M 5/3158* (2013.01); *A61M 5/3204* (2013.01); *A61M 5/3202* (2013.01); *A61M 2205/43* (2013.01); *A61M 2205/581* (2013.01); *A61M 2205/582* (2013.01)

(58) Field of Classification Search
CPC .... A61M 2005/208; A61M 2005/3267; A61M 2205/43; A61M 2205/581
See application file for complete search history.

(56) References Cited

U.S. PATENT DOCUMENTS

| | | |
|---|---|---|
| 2004/0210199 A1 | 10/2004 | Atterbury |
| 2006/0069382 A1* | 3/2006 | Pedersen ............ A61K 9/0004 604/890.1 |
| 2009/0012479 A1 | 1/2009 | Moller et al. |
| 2011/0238014 A1 | 9/2011 | Maritan |
| 2012/0310206 A1 | 12/2012 | Kouyoumjian et al. |
| 2013/0041327 A1 | 2/2013 | Daniel |
| 2013/0090605 A1 | 4/2013 | O'Connor et al. |
| 2013/0317435 A1 | 11/2013 | Fabien et al. |
| 2013/0345642 A1 | 12/2013 | Cowe |
| 2014/0163477 A1 | 6/2014 | Quinn et al. |
| 2014/0371670 A1* | 12/2014 | Holmqvist ............ A61M 5/20 604/82 |
| 2015/0165129 A1 | 6/2015 | Row et al. |
| 2015/0209518 A1 | 7/2015 | Moser et al. |
| 2015/0283323 A1 | 10/2015 | Young et al. |
| 2016/0008542 A1 | 1/2016 | Hirschel et al. |
| 2016/0085425 A1 | 3/2016 | O'Leary et al. |
| 2016/0193412 A1 | 7/2016 | Cereda et al. |
| 2017/0119972 A1 | 5/2017 | Holmqvist |

FOREIGN PATENT DOCUMENTS

| | | |
|---|---|---|
| CN | 104519929 | 4/2015 |
| EP | 2489380 | 8/2012 |
| EP | 2722065 | 4/2014 |
| JP | 2015-536162 | 12/2015 |
| JP | 2016-512766 | 5/2016 |
| JP | 2017-501752 | 1/2017 |
| RU | 2012137269 | 3/2014 |
| WO | WO 2006/079481 | 8/2006 |
| WO | WO 2011/039233 | 4/2011 |
| WO | WO 2011/123024 | 10/2011 |
| WO | WO 2013/057033 | 4/2013 |
| WO | WO 2013/057034 | 4/2013 |
| WO | WO 2014/005808 | 1/2014 |
| WO | WO 2014/060563 | 4/2014 |
| WO | WO 2014/146209 | 9/2014 |
| WO | WO 2015/004050 | 1/2015 |
| WO | WO 2015/055588 | 4/2015 |

OTHER PUBLICATIONS

PCT International Preliminary Report on Patentability in International Application No. PCT/EP2016/062504, dated Dec. 5, 2017, 6 pages.

* cited by examiner

DRUG DELIVERY DEVICE WITH AUDIBLE INDICATOR SPRING

CROSS REFERENCE TO RELATED APPLICATIONS

The present application is a continuation of U.S. application Ser. No. 15/578,881 (now U.S. Pat. No. 10,888,669), filed on Dec. 1, 2017, which is the national stage entry of International Patent Application No. PCT/EP2016/062504, filed on Jun. 2, 2016, and claims priority to Application No. EP 15170583.7, filed in on Jun. 3, 2015, the disclosures of which are expressly incorporated herein in entirety by reference thereto.

TECHNICAL FIELD

The disclosure relates to a drug delivery device.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by a plunger which is continuously pressed during the injection. There are numerous disadvantages associated with this approach. For example, if the plunger is released prematurely, the injection will stop and may not deliver an intended dose. Furthermore, the force required to push the plunger may be too high (e.g., if the user is elderly or a child). And, aligning the injection device, administering the injection, and keeping the injection device still during the injection may require dexterity which some patients may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Furthermore, it is necessary to administer the full dose in order to achieve full effectiveness of the medicament within the patient.

Thus, there remains a need for an improved drug delivery device.

SUMMARY

Exemplary embodiments of the disclosure are given in the dependent claims.

According to the present disclosure, a drug delivery device, e. g. a manual injection device or an autoinjector, comprises: a case adapted to hold a medicament container, a plunger disposed within the case and slidable from a proximal position into a distal position for delivering a medicament from the medicament container, an audible indicator that is arranged within a case pocket lateral to the plunger and that is in operative connection with the plunger, the audible indicator comprises at least one indicator spring and at least one locking element, wherein the indicator spring is biased by the locking element and the indicator spring relaxes due to a release of the locking element by a movement of the plunger.

The provided drug delivery device is improved due to the audible indicator which can be used for indicating to a patient or user that the full dose of medicament was spent. The arrangement of the audible indicator within a case pocket lateral to the plunger allows extended configuration options of the drug delivery device with respect to the prior art. This is due to the fact that the audible indicator may arranged into the device at the end of assembly or afterwards. A configuration of the audible indicator may thus be variably adaptable onto the requirements of the device. Moreover, the assembly of the drug delivery device is easy to perform due to this arrangement of the audible indicator.

In an exemplary embodiment, the drug delivery device is provided with a case pocket that is adapted to receive an audible indicator. The drug delivery device may thus be either provided with an audible indicator or not if required.

In a further exemplary embodiment, the indicator spring relaxes in a distal direction with respect to the case. The indicator spring may then hit the case due to the relaxation in the distal direction, thereby generating an audible and tactile feedback.

In an exemplary embodiment, the indicator spring includes a coil spring, e.g. a helical compression spring. The coil spring may be formed by a solid steel wire and is thus mechanically robust.

Furthermore, the indicator spring may comprise a proximal end and a distal end, wherein the proximal end is fixed to the case and the distal end is supportable by the locking element. The case pocket may be provided within a case component in which the indicator spring is inserted. If the indicator spring is compressed fully, its length is sufficiently short to fit into the case pocket; then, once expanded, the ends of the indicator spring expand into the closed sections of the case pocket. Once the drug delivery device is fully assembled, a second case component additionally closes the case pocket. The proximal end of the indicator spring may be fixed to the case by an adhesive bonding. The fixing is however not required as the indicator spring is in compression, i.e. the indicator spring exerts a compressive force against both the case and locking element.

In an exemplary embodiment, the locking element may be configured as a flexible arm, wherein the locking element is biased by the plunger.

The locking element may be biased radially outwards by the plunger. For example, the locking element abuts against an outer circumference of the plunger and is prevented from deflecting radially inwards by the plunger.

As long as the locking element is biased radially outwards, the locking element supports the distal end of the coil spring. Thus, the coil spring is not allowed to relax as long as the plunger is not in the distal position and the medicament is still in the medicament container.

In an exemplary embodiment, the locking element comprises a projection for supporting the coil spring, wherein the distal end of the coil spring abuts against the projection as long as the locking element is biased radially outwards.

In a further exemplary embodiment, the locking element is released when the plunger is in the distal position. In the distal position, the locking element does not abut against the outer circumference of the plunger anymore and is thus allowed to release in a radial inward direction. When the locking element releases radially inwards, the indicator spring relaxes, wherein the distal end of the indicator spring hits a contact surface arranged on the case, thereby generating noise as a recognizable audible signal.

In an exemplary embodiment, the drug delivery device comprises a plurality of indicator springs. For example, the indicator springs are arranged around a circumference within the case.

Furthermore, the case may comprise a front case and a rear case which is surrounded by the front case along a longitudinal direction and adapted to close an open proximal end of the front case. The indicator spring may be arranged within the rear case.

In an exemplary embodiment, the drug delivery device is configured as an autoinjector that comprises a needle shroud telescopically coupled to the case, a shroud spring biasing the needle shroud distally relative to the case, and a drive spring biasing the plunger from the proximal position towards the distal position.

The drive spring may be arranged in parallel to the indicator spring.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given herein below and the accompanying drawings which are given by way of illustration only, and thus, are not limitative of the present disclosure, and wherein.

Corresponding parts are marked with the same reference symbols in all figures.

DETAILED DESCRIPTION

Figure 1:
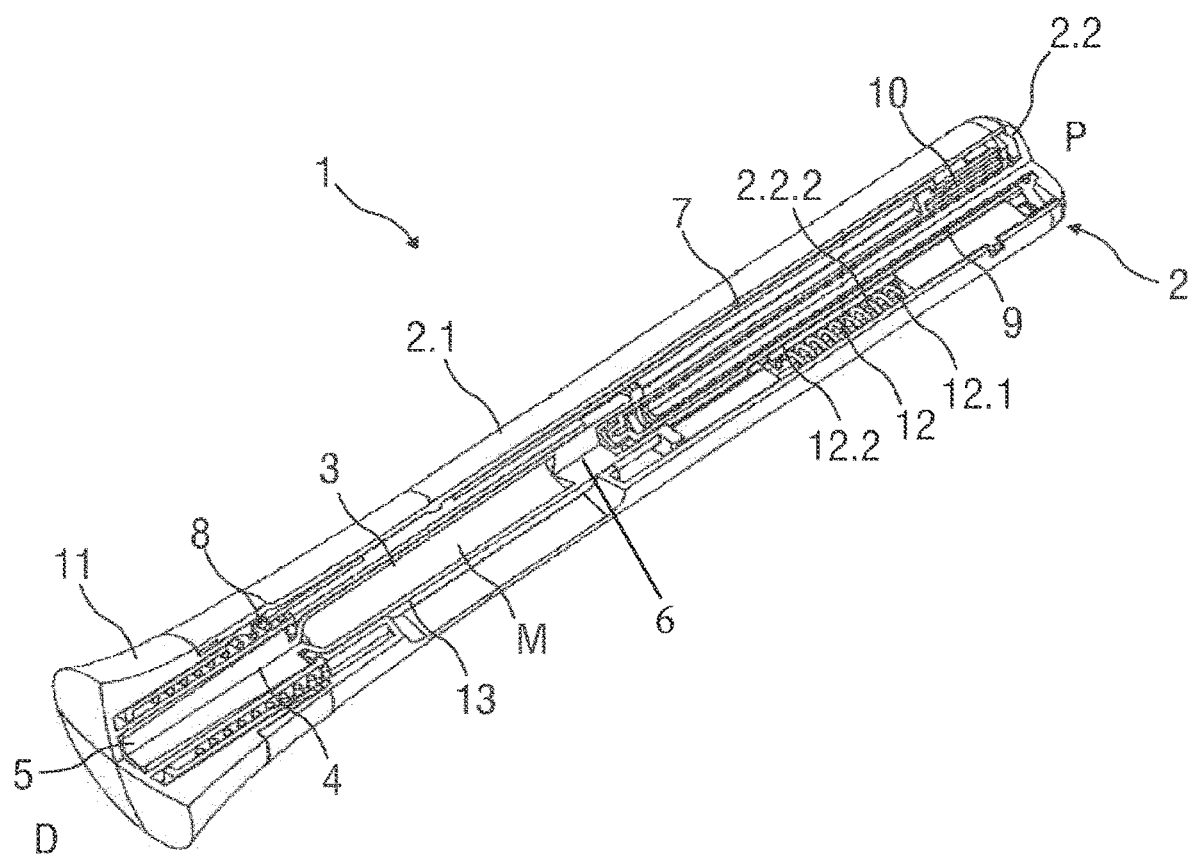
FIG. 1 is a schematic perspective partial section of an exemplary embodiment of a drug delivery device according to the present disclosure.

FIG. 1 shows a schematic perspective partial section of an exemplary embodiment of a drug delivery device 1 according to the present disclosure.

In the shown exemplary embodiment, the drug delivery device 1 is configured as an autoinjector device.

The drug delivery device 1 comprises a case 2 with a front case 2.1 and a rear case 2.2. The case 2 is adapted to hold a medicament container 3, such as a syringe. The medicament container is referred to hereinafter as the "syringe 3". The syringe 3 may be a pre-filled syringe containing a medicament M and having a needle 4 arranged at a distal end of the syringe 3. In another exemplary embodiment, the medicament container 3 may be a cartridge which includes the medicament M and engages a removable needle (e.g., by threads, snaps, friction, etc.).

The drug delivery device 1 further comprises a protective needle sheath 5 that is coupled to the needle 4. For example, the protective needle sheath 5 is removably coupled to the needle 4. The protective needle sheath 5 may be a rubber needle sheath or a rigid needle sheath which is composed of rubber and a full or partial plastic shell.

For sealing the syringe 3 proximally and for displacing a medicament M contained in the syringe 3 through the needle 4, a stopper 6 is provided and arranged within the syringe 3.

A needle shroud 7 is telescopically coupled to the case 2 and movable between a first extended position relative to the case 2 in which the needle 4 is covered and a retracted position relative to the case 2 in which the needle 4 is exposed. Furthermore, a shroud spring 8 is arranged to bias the needle shroud 7 distally against the case 2.

In the shown exemplary embodiment, a drive spring 9 is arranged within the case 2. A plunger 10 serves for forwarding a force of the drive spring 9 to the stopper 6. The plunger 10 may be hollow, wherein the drive spring 9 is arranged within the plunger 10 biasing the plunger 10 distally against the case 2. In another exemplary embodiment, the plunger 10 may be solid and the drive spring 9 may engage a proximal end of the plunger 10.

The plunger 10 is movable from a proximal position (shown in FIG. 1) towards a distal position relative to the case 2 to drive the medicament M from the syringe 3 through the needle 4 into the patient.

Furthermore, the plunger 10 may be prevented from releasing prior to retraction of the needle shroud 7 relative to the case 2. The plunger 10 may be configured to be released once the needle shroud 7 is sufficiently retracted. This is realized by a plunger release mechanism, which will not be described in more detail.

A cap 11 may be removably disposed at a distal end of the case 2, in particular at a distal end of the front case 2.1. The cap 11 may comprise grip features (not shown in detail) for facilitating a removal of the cap 11, e.g., by twisting and/or pulling the cap 11 off the case 2 and for engaging the protective needle sheath 5, the case 2 and/or the needle shroud 7. The grip features may include a barb, a hook, a narrowed section, etc.

As long as the cap 11 is in place, the needle shroud 7 is prevented from retracting relative to the case 2, thereby avoiding unintentional activation of the drug delivery device 1, e.g., if dropped, during shipping or packaging, etc. This is realized by a shroud lock mechanism, which will not be described in more detail.

The drug delivery device 1 further comprises at least one audible indicator 12 for producing an audible feedback for a user or patient indicating completion of medicament M delivery. In other words: The audible indicator 12 is provided to indicate to a user or a patient that the full dose of medicament M was spent.

According to the exemplary embodiment, the drug delivery device 1 comprises one audible indicator 12 that is arranged within the rear case 2.2.

The audible indicator 12 comprises an indicator spring 12.1 and a locking element 12.2.

Figure 2:
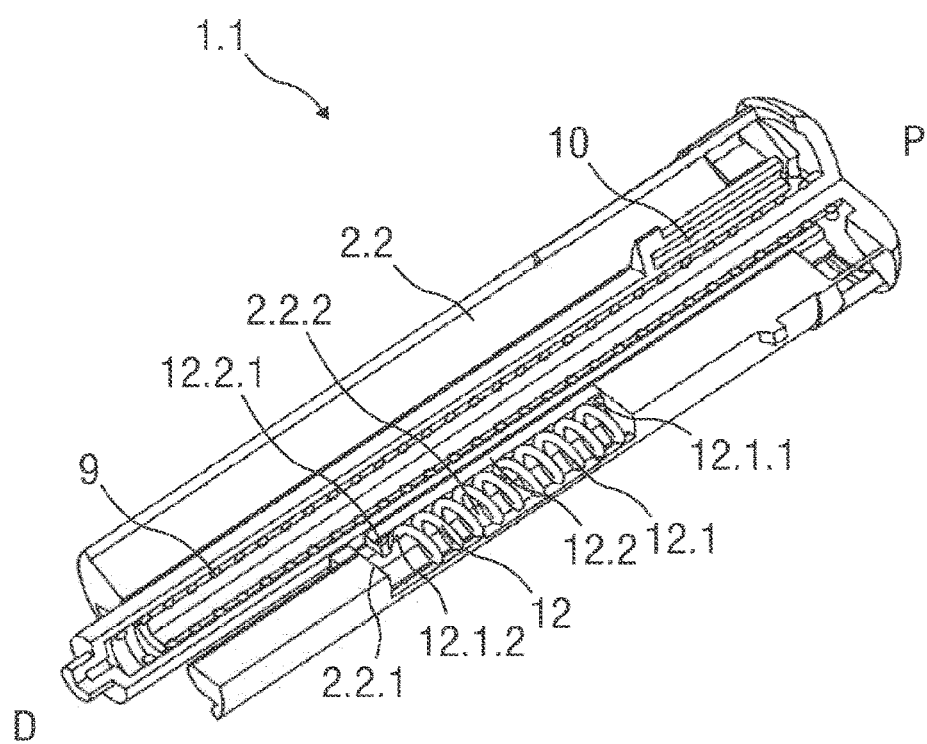
FIG. 2 is a schematic perspective partial section of an exemplary embodiment of a drive sub assembly comprising a rear case with a plunger and an audible indicator, wherein the plunger is in a proximal position.

The indicator spring 12.1 may be configured as a coil spring as it is shown in the present FIGS. 1 and 2. For example, the indicator spring 12.1 is made from a solid steel wire comprising a number of coils. The indicator spring 12.1 comprises a proximal end 12.1.1 that is fixed to a stop arranged within the rear case 2.2. A distal end 12.1.2 of the indicator spring 12.1 is supported by a projection 12.2.1 arranged on the locking element 12.2. Furthermore, the indicator spring 12.1 may be arranged within a case pocket 2.2.2 provided within the rear case 2.2. If the indicator spring 12.1 is compressed fully, its length is sufficiently short to fit into the case pocket 2.2.2; then, once expanded, the ends 12.1.1, 12.1.2 of the indicator spring 12.1 expand into the closed sections of the case pocket 2.2.2 (not illustrated). Once the drug delivery device 1 is fully assembled, a not shown case component may additionally close the case pocket 2.2.2.

The case pocket 2.2.2 also receives the locking element 12.2 that may be configured as a flexible arm that is biased radially outwards by an outer circumference of the plunger 10. Thus, the locking element 12.2 abuts against the plunger 10 as long as the plunger 10 is not in the distal position relative to the case 2.

Figure 3:
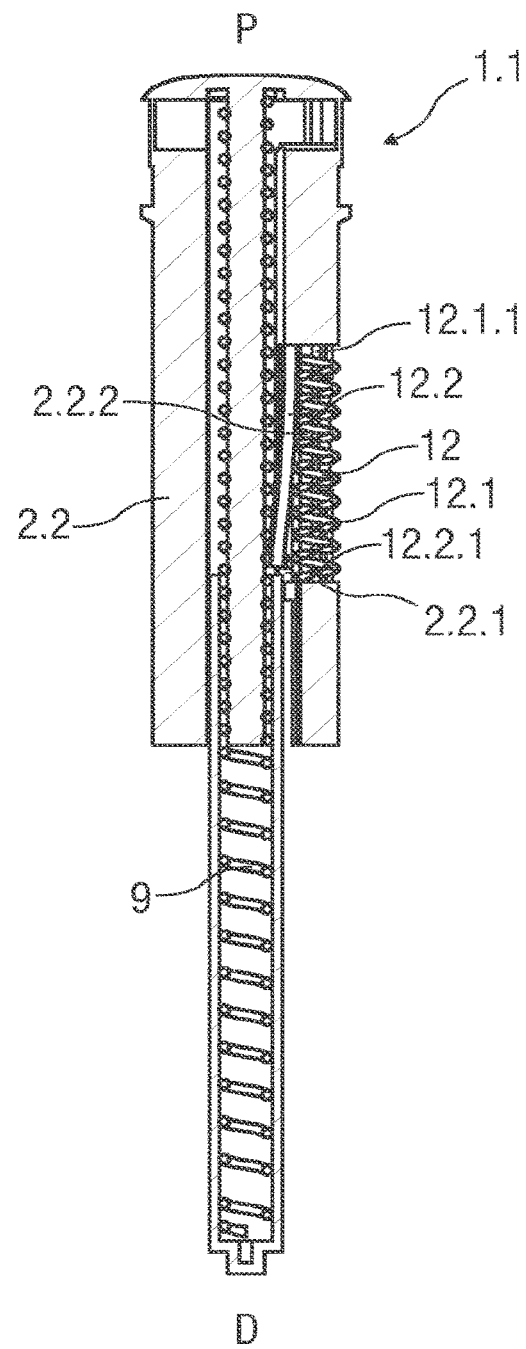
FIG. 3 is a schematic longitudinal section of the drive subassembly with the plunger in a distal position.

As it can be best seen in FIGS. 2 and 3, the case pocket 2.2.2 and thus the audible indicator 12 are arranged lateral to the plunger 10. This allows extended configuration options of the drug delivery device 1 due to the fact that the audible indicator 12 may be arranged into the case pocket 2.2.2 at the end of an assembly process or even afterwards. A configuration of the audible indicator 12 may thus be variably adaptable onto the requirements of the drug delivery device 1. It is also possible to either provide the drug delivery device 1 with an audible indicator 12 or not.

The projection 12.2.1 projects radially outwards from the locking element 12.2 and thus in a radial direction away from the plunger 10. The projection 12.2.1 creates a stop for the distal end 12.1.2 of the indicator spring 12.1, which is biased in the distal direction D due to the abutment on the projection 12.2.1.

The abutment of the locking element 12.2 and the plunger 10 is releasable by moving the plunger 10 in the distal direction D relative to the case 2, wherein the locking element 12.2 is allowed to relax radially inwards when the plunger 10 reaches its distal position, wherein a proximal end of the plunger 10 is distally behind the locking element 12.2. When the locking element 12.2 relaxes radially inwards, the abutment of the distal end 12.1.2 of the indicator spring 12.1 and the projection 12.2.1 is released, thus allowing the biased indicator spring 12.1 to relax in the distal direction D. As a result, the distal end 12.1.2 of the indicator spring 12.1 hits a contact surface 2.2.1 arranged on the rear case 2.2. The hitting noise generates an audible and tactile indication signal to a user that the full dose of medicament was spent.

In an exemplary embodiment, the drug delivery device 1 may be formed from at least two subassemblies, e.g., a control or front subassembly (not illustrated) and a drive or rear subassembly 1.1, to allow for flexibility as to the time and location of manufacture of the subassemblies 1.1 and final assembly with the syringe 3.

FIG. 2 shows a schematic perspective partial section of an exemplary embodiment of such a drive sub assembly 1.2 with the plunger 10 in the proximal position. FIG. 3 is a schematic longitudinal section of the drive subassembly 1.1 with the plunger 10 in the distal position.

The drive sub assembly 1.1 comprises the plunger 10, the drive spring 9, the rear case 2.2 and the audible indicator 12.

The front sub assembly (not shown separately) comprises at least the front case 2.1, the needle shroud 7 and a syringe carrier 13 into which the syringe 3 is assembled.

After final assembly of the drug delivery device 1, the drive sub assembly 1.1 is mounted onto the front sub assembly.

The skilled person readily understands that application of the audible indicator 12 is not limited to autoinjector devices. Instead, the audible indicator 12 may likewise be applied in a manually operated drug delivery device 1 for indicating that the plunger 10 has been completely moved into the distal position.

In an exemplary embodiment, the audible indicator 12 may produce an audible signal with a volume of at least 100 dB(A), e.g. measured at a distance of approximately 150 mm. In a test setup, the drug delivery device 1 was placed in a sound-absorbing environment on a table with the needle shroud 7 ahead. An elastomeric layer was located between the needle shroud 7 and the table to acoustically decouple the drug delivery device 1 from the table. Two microphones (e.g. ROGA MI-17 (IEPE)) were placed laterally from the drug delivery device 1 opposite each other at a distance of 150 mm, respectively and 170 mm above the table. A first test was performed with a user holding and operating the drug delivery device 1 with the right hand closed around the drug delivery device 1, wherein the fingers of the hand covered one side of the drug delivery device 1 directed towards one of the microphones and wherein the opposite side pointing towards the other microphone was covered by the palm of the hand. The volume of the audible signal on the finger side microphone was at least 100 dB(A) while the volume on the palm side microphone was lower than 100 dB(A). Another test was performed with a user holding and operating the drug delivery device 1 only with the fingertips of the right hand, wherein the palm of the hand was located between the drug delivery device 1 and one of the microphones; however, the drug delivery device 1 was not touched by the palm. The volume of the audible signal acquired by both microphones was at least 100 dB(A), wherein the volume detected by the palm side microphone was slightly lower than the volume detected by the other microphone.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
1.1 drive subassembly
2 case
2.1 front case
2.2 rear case
2.2.1 contact surface
2.2.2 case pocket
3 medicament container (syringe 3)
4 needle
5 protective needle sheath
6 stopper
7 needle shroud
8 shroud spring
9 drive spring
10 plunger
11 cap
12 audible indicator
12.1 indicator spring
12.1.1 proximal end
12.1.2 distal end
12.2 locking element
12.2.1 projection
13 syringe carrier
D distal direction
M medicament
P proximal direction

The invention claimed is:

1. A drug delivery device comprising:
a case adapted to hold a medicament container;
a plunger disposed within the case and slidable from a proximal position into a distal position for delivering a medicament from the medicament container;
an audible indicator that is arranged within the case lateral to the plunger and that is configured to be in operative connection with the plunger; and
a drive spring biasing the plunger from the proximal position towards the distal position,
wherein the plunger is hollow and the drive spring is arranged within the plunger,
wherein the audible indicator comprises at least one indicator element and at least one support element,
wherein the at least one indicator element is configured to be supported by the at least one support element in a supported state,
wherein in a non-supported state, the at least one indicator element is configured to be in a deformed state relative to a shape of the at least one indicator element in the supported state due to a release of the at least one support element from the at least one indicator element by a movement of the plunger,
wherein the at least one support element comprises a projection for supporting the at least one indicator element,
wherein the projection of the at least one support element projects radially outwards from a remainder of the at least one support element,
wherein the at least one support element is configured as a flexible arm, and
wherein the at least one support element is configured to be in abutment with the plunger in the supported state.

2. The drug delivery device according to claim 1, wherein the at least one indicator element is configured to relax in a distal direction with respect to the case.

3. The drug delivery device according to claim 2, wherein the at least one indicator element is configured to hit the case due to the relaxation in the distal direction, thereby generating an audible feedback.

4. The drug delivery device according to claim 1, wherein the at least one indicator element comprises a proximal end and a distal end, wherein at least one of the following is fulfilled:
the at least one indicator element is fixed or stationary to the case or
the distal end is supportable by the at least one support element.

5. The drug delivery device according to claim 1, wherein the abutment of the at least one support element with the plunger is an abutment of the at least one support element with an outer circumference of the plunger.

6. The drug delivery device according to claim 5, wherein a distal end of the at least one indicator element is configured to be supported by the at least one support element as long as the at least one support element is held radially outwards by the abutment of the at least one support element with the plunger.

7. The drug delivery device according to claim 6, wherein the distal end of the at least one indicator element is configured to abut against the projection as long as the at least one support element is held radially outwards.

8. The drug delivery device according to claim 1, wherein the at least one support element and the plunger are configured such that the abutment of the at least one support element with the plunger is released when the plunger is in the distal position.

9. The drug delivery device according to claim 1, wherein the case comprises a front case and a rear case, the rear case being surrounded by the front case along a longitudinal direction and adapted to close an open proximal end of the front case.

10. The drug delivery device according to claim 9, wherein the flexible arm has a proximal end that is fixed to the rear case or is stationary with regard to the rear case.

11. The drug delivery device according to claim 9, wherein a case pocket is arranged within the rear case.

12. The drug delivery device according to claim 11, wherein the drug delivery device is configured as an auto-injector device further comprising:
a needle shroud telescopically coupled to the case, and
a shroud spring biasing the needle shroud distally relative to the case.

13. The drug delivery device according to claim 12, wherein the audible indicator is arranged within the case pocket.

14. The drug delivery device according to claim 1, wherein the drive spring is arranged in parallel and radially offset to the at least one indicator element.

15. The drug delivery device according to claim 14, wherein the at least one indicator element extends only partially around a circumference of the plunger.

16. The drug delivery device according to claim 14, wherein the drug delivery device is configured such that the audible indicator can be used for indicating to a patient or a user that a full dose of medicament was spent.

17. The drug delivery device according to claim 1, wherein the at least one support element is configured to abut against an outer circumference of the plunger, and
wherein the at least one support element is configured to be prevented from deflecting radially inwards by the plunger.

18. The drug delivery device according to claim 1, wherein the at least one indicator element is configured to be not allowed to deform as long as the plunger is not in the distal position.

19. The drug delivery device according to claim 1, wherein the drug delivery device comprises the medicament container, and the medicament container contains the medicament.

20. The drug delivery device according to claim 1, wherein the projection is arranged on a distal end of the at least one support element.

21. A system comprising:
a plunger slidable from a proximal position into a distal position for delivering a medicament from a medicament container, the plunger being hollow;
a drive spring biasing the plunger from the proximal position towards the distal position, the drive spring arranged within the plunger; and
an audible indication mechanism comprising:
at least one indicator element configured to be arranged in a position lateral to the plunger and configured to produce an audible signal; and
at least one support element comprising a projection for supporting the at least one indicator element,
wherein the at least one indicator element is configured to be supported by the at least one support element in a supported state,
wherein in a non-supported state, the at least one indicator element is configured to be in a deformed state relative to a shape of the at least one indicator element in the supported state due to a release of the at least one support element from the at least one indicator element by a movement of the plunger,
wherein the projection of the at least one support element projects radially outwards from a remainder of the at least one support element,
wherein the at least one support element is configured as a flexible arm, and
wherein the at least one support element is configured to be in abutment with the plunger in the supported state.

22. A method for indicating a completion of delivering a medicament using a drug delivery device, wherein the drug delivery device comprises:
a case adapted to hold a medicament container;
a plunger disposed within the case and slidable from a proximal position into a distal position for delivering the medicament from the medicament container;
an audible indicator that is arranged within the case lateral to the plunger and that is configured to be in operative connection with the plunger; and
a drive spring biasing the plunger from the proximal position towards the distal position,
wherein the plunger is hollow and the drive spring is arranged within the plunger,
wherein the audible indicator comprises at least one indicator element and at least one support element,
wherein the at least one indicator element is configured to be supported by the at least one support element in a supported state,
wherein in a non-supported state, the at least one indicator element is configured to be in a deformed state relative to a shape of the at least one indicator element in the supported state due to a release of the at least one support element from the at least one indicator element by a movement of the plunger,
wherein the at least one support element comprises a projection for supporting the at least one indicator element,
wherein the projection of the at least one support elements projects radially outwards from a remainder of the at least one support element,
wherein the at least one support element is configured as a flexible arm, and
wherein the at least one support element is configured to be in abutment with the plunger in the supported state,
wherein the method comprises:
sliding the plunger from the proximal position into the distal position using the drive spring to deliver the medicament from the medicament container; and
releasing the at least one support element from the at least one indicator element as the plunger slides from the proximal position to the distal position such that the at least one indicator element transitions from the supported state to the deformed state.

* * * * *